US00PP12172P2

(12) United States Plant Patent
Dean et al.

(10) Patent No.: US PP12,172 P2
(45) Date of Patent: Oct. 30, 2001

(54) GERANIUM HYBRID PLANT NAMED 'PINK SPICE'

(75) Inventors: Mark Dean; Esme Julien Dean, both of Oropi (NZ)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 09/274,028

(22) Filed: Mar. 22, 1999

(51) Int. Cl.[7] ..... A01H 5/00

(52) U.S. Cl. ..... Plt./324

(58) Field of Search ..... Plt./324

(56) References Cited

PUBLICATIONS

UPOV–ROM GTITM Computer Database 2000/04, GTI Jouve Retrieval Software, citations for 'Pink Spice'.*
Internet website http://www.elizabethscottage.com/FeatureArchive/May2000–feature.html, May 2000.*
Internet website http://216/187.74.156/news/top_2000.html, May 4, 2001.*

* cited by examiner

*Primary Examiner*—Bruce R. Campell
*Assistant Examiner*—Anne Marie Grunberg
(74) *Attorney, Agent, or Firm*—Klarquist Sparkman LLP

(57) ABSTRACT

A new and distinct selection of true Geranium, which shall be referred to hereinafter as cultivar Pink Spice. Cultiver Pink Spice differs distinctively from other Geranium plants by possessing a unique combination of rosette growth habit with purplish green foliage and large deep pink flowers.

1 Drawing Sheet

BACKGROUND OF THE INVENTION

This invention relates to a new and distinct selection of Geranium, a member of the Geraniaceae family. Cultivar 'Pink Spice' was discovered as a seedling in a cultivated area of a Nursery in Tauranga, New Zealand. *Geranium traversii* var. *elegans* Cockayne and *Geranium sessiliflorum* Cavanilles were grown at this Nursery and this new selection was produced by open pollination of these two species. Seed was collected off of these open pollinated plants and sown the next season. When these seedlings flowered, seedlings were selected again. This process was repeated for three years, from 1989 to 1991, until a final selection was made which had large deep pink flowers and purplish green foliage.

SUMMARY OF INVENTION

Geranium hybrid cultivar 'Pink Spice' combines the best horticultural traits from both parents. The rosette, bushy growth habit is typical of these two parents which are both classified in the Sessiliflorum Group. One parent, *Geranium traversii* var. *elegans* has green foliage and light pink flowers. The other parent, *Geranium sessiliflorum* has bronze purplish colored foliage with white flowers. Though some seedlings exhibited a more distinct purple colored leaf, my selection was chosen for the large deep pink flowers along with the ligher purple hue in the foliage.

BRIEF DESCRIPTION OF DRAWINGS

The photograph of the discovery shows the overall growth habit and foliage color.

Another photograph displays a close-up of the flowers and foliage. Below is a detailed description of the Geranium hybrid cultivar 'Pink Spice.' Color designations refer to the R.H.S. Colour Chart published by The Royal Horticulture Society of London. Plant size and description are based on plants ages two years growing in Azusa, Calif. These plants have been asexually propagated by cuttings in Azusa, Calif.

Overall size: Height varies dependent upon climatic exposure and soil. A plant in a 15-cm wide container in full sun measures about 6 cm tall and 24 cm wide, not including runners. A plant in partial shade in unrestricted growing space measures about 24 cm tall and 52 cm wide. The height to width ratio is double in unrestricted growing space.

Overall habit: Evergreen perennial rosette growth habit. Foliage surrounds the plant producing a symmetrical rounded habit. In full sun, foliage is smaller. In partial shade, larger foliage is produced. In either exposure the symmetrical rounded outline is retained. Low, spreading habit is the result of seasonal runners arising from the center of the plant and spreading in equal distance. These runners can measure up to about 60–70 cm in length in unrestricted growing areas. These runners appear in spring and die off by winter.

Foliage:

*Shape.*—Orbicular; lobed halfway down leaf blade into seven segments; each segment further divided by 3 shallow secondary lobes.

*Length.*—Mature — varies 3.5 cm to 4.5 cm; Juvenile — smaller than above.

*Width.*—Mature — varies 4.0 cm to 5.5 cm. Juvenile — smaller than above.

*Arrangement.*—Opposite.

*Surface.*—Veination: Deeply reticulated. Upper: Lightly pubescent, slightly shine. Lower: Pubescent.

*Color.*—Upper mature: Green Group 137A & 139A and Red-Purple Group 59A. Individual leaves may be one color, or a mixture of colors in a continuous variation or splotching pattern across the leaf. Winter: Colors listed above mixed with the following mottled. colors: Orange group 28A, Red Group 45D, and Green-Yellow Group 1D. Lower Mature:

Yellow-Green Group 146B. Lower Veination: Red-Purple Group 59C. Upper Juvenile: Purple Group 79D mixed with Red-Purple Group 59C in veination. Lower Juvenile: Yellow-Green Group 147B.

*Petiole.*—Length: Mature — varies 7.5 cm to 18.5 cm in length. Juvenile — Less than 5 cm in length. Surface: Pubescent. Thickness: varies between 2–3 mm. Color: Red-Purple Group 59D.

Texture: Semi-coriaceous.

Margins: Crenate.

Stem:

*Habit.*—Low-creeping on the ground, unexposed, clothed by foliage.

*Color.*—Red-Purple Group 66D.

*Pubescence.*—Silky pubescence.

Stipule:

*Size.*—4–7 mm in length; 4 mm wide.

*Apex.*—Long acuminate.

*Color.*—Red-Purple Group 66D, edges transparent.

Flower:

*Arrangement.*—1-flowered.

*Peduncle.*—About 2.5 cm to 4.0 cm long; color: Red-Purple Group 62D.

*Type.*—Single form; erect, funnel-shaped.

*Size.*—Diameter — about 1.5 cm to 2.0 cm wide; overall height of flowers maximum of about 3.0 to 4.0 cm above foliage; corolla height — about 0.5 cm to 1.0 cm.

*Petals.*—Consistently 5 in number. Shape: Broadly spatulate. Margins: Entire, undulate, and recurved. Length: approximately 1 cm. Width: approximately 1 cm. Color: Upper side of petals — margins Purple Group 77D, slightly darkening to a Purple Group 77B on central area of petal, inner throat Green-White Group 157A, 5–7 prominent guide-marks per petal, translucent veins within base. Under side of petals — margins variable Red — Purple Group 74C and 74B.

*Calyx.*—Composed of 5 overlapping sepals. Color: Greyed — Orange Group 166A. Shape: Elliptical prominent apical tip. Size: 7 mm long and 4 mm wide.

*Reproductive.*—Stamens: 10, arranged in 2 whorls, two-thirds the length of the sepals. Stigma: 5 stigma, two-thirds the length of the sepals. Fruit and Seed Production: None observed to date in Azusa, Calif.

Pest & disease: No known disease has been seen on my new selection.

We claim:

1. A new and distinct selection of Geranium plant as substantially shown and described herein, that is characterized particularly as a novelty by the unique combination of rosette growth habit with purplish-green foliage and large deep pink flowers.

* * * * *

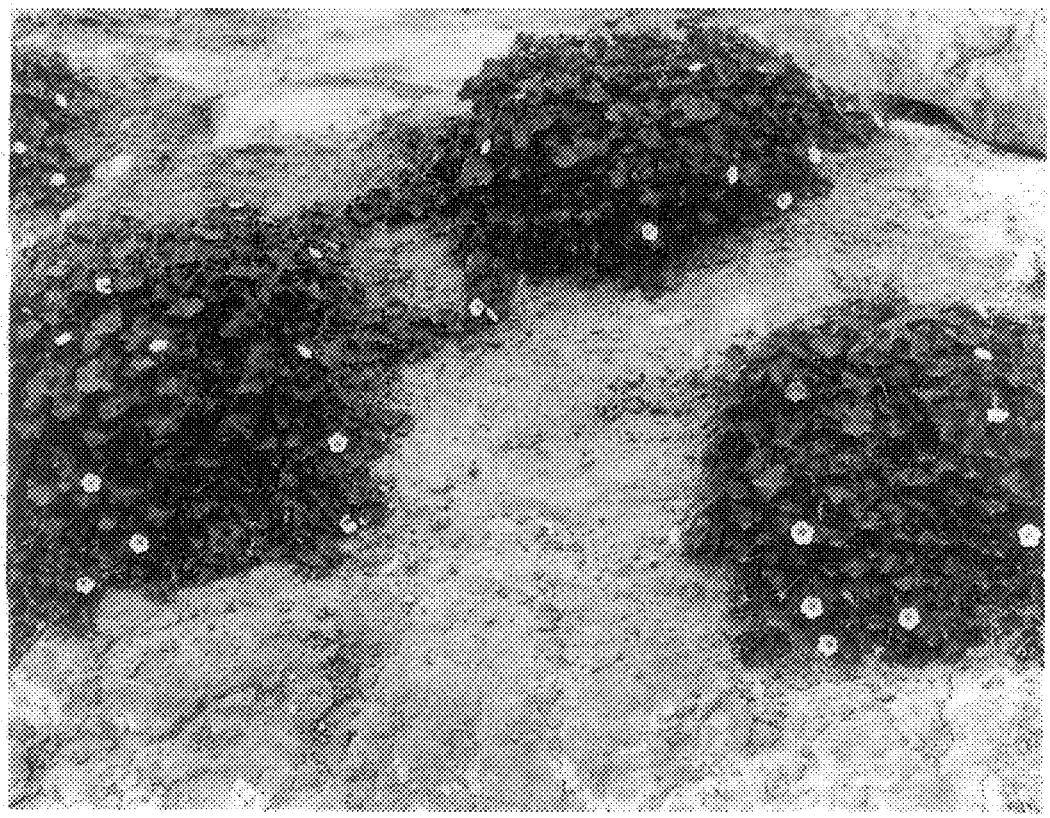
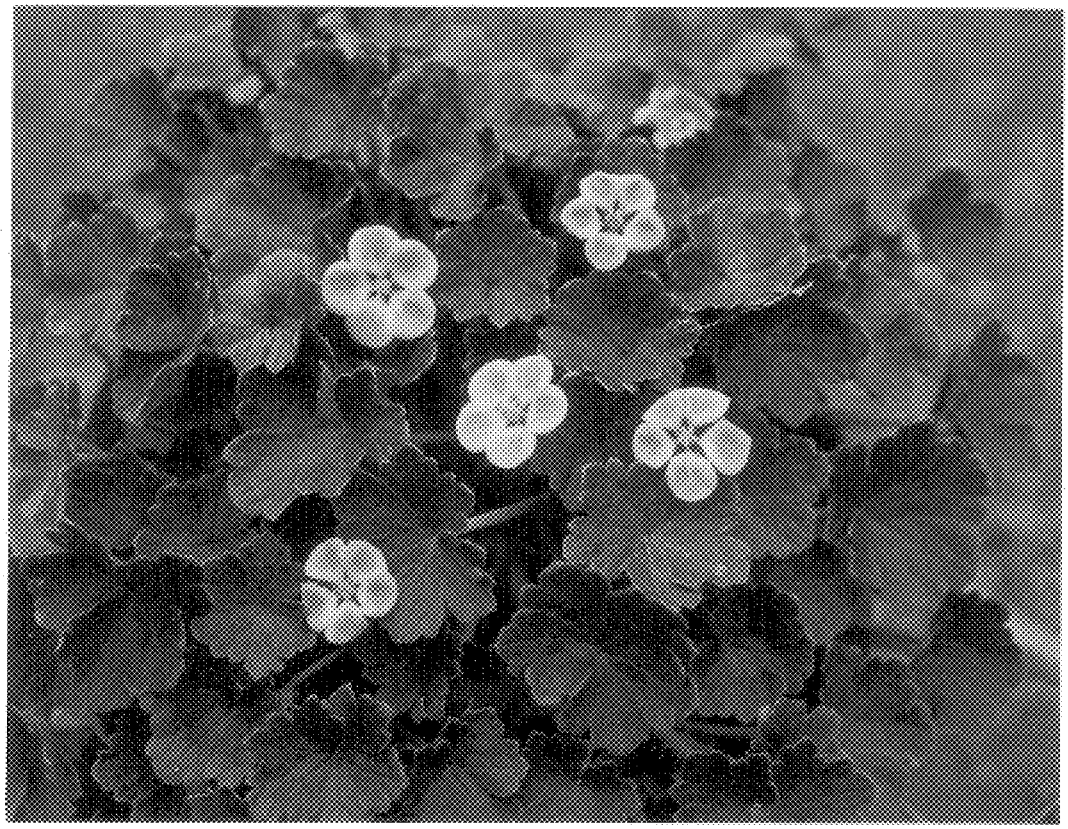

UNITED STATES PATENT AND TRADEMARK OFFICE

CERTIFICATE OF CORRECTION

PATENT NO. : PP 12,172 P2
DATED : October 30, 2001
INVENTOR(S) : Mark Dean and Esme Julien Dean It is certified that error appears in the above-identified patent and that said Letters Patent is hereby corrected as shown below:

Column 2,
Line 1, “ages” should read -- aged --.

Signed and Sealed this

Twenty-fourth Day of September, 2002

*Attest:*

*Attesting Officer*

JAMES E. ROGAN
*Director of the United States Patent and Trademark Office*